United States Patent
Prashad et al.

(10) Patent No.: US 7,452,999 B2
(45) Date of Patent: Nov. 18, 2008

(54) CHEMICAL PROCESS FOR THE PREPARATION OF INTERMEDIATES TO OBTAIN N-FORMYL HYDROXY-LAMINE COMPOUNDS

(75) Inventors: Mahavir Prashad, Montville, NJ (US); Hong-Yong Kim, Whippany, NJ (US); Bin Hu, Green Brook, NJ (US); Joel Slade, Flanders, NJ (US); Prasad Koteswara Kapa, Parsippany, NJ (US); Michael John Girgis, Montville, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/544,919

(22) PCT Filed: Feb. 20, 2004

(86) PCT No.: PCT/US2004/005159

§ 371 (c)(1),
(2), (4) Date: Apr. 24, 2007

(87) PCT Pub. No.: WO2004/076053

PCT Pub. Date: Sep. 10, 2004

(65) Prior Publication Data

US 2007/0179298 A1    Aug. 2, 2007

Related U.S. Application Data

(60) Provisional application No. 60/449,017, filed on Feb. 21, 2003, provisional application No. 60/449,016, filed on Feb. 21, 2003, provisional application No. 60/449,015, filed on Feb. 21, 2003.

(51) Int. Cl.
| C07D 417/00 | (2006.01) |
| C07D 401/00 | (2006.01) |
| C07D 277/00 | (2006.01) |
| C07D 207/00 | (2006.01) |
| C07D 405/00 | (2006.01) |
| C07D 317/44 | (2006.01) |

(52) U.S. Cl. .................. 548/200; 548/518; 548/526; 546/269.7; 546/278.4; 546/279.1; 549/439

(58) Field of Classification Search ............... None
See application file for complete search history.

(56) References Cited

U.S. PATENT DOCUMENTS

| 6,423,690 | B1 | 7/2002 | Davies et al. |
| 6,576,772 | B1 | 6/2003 | Zhang |
| 6,797,820 | B2 | 9/2004 | Patel et al. |
| 6,852,752 | B2 | 2/2005 | Jacobs et al. |
| 6,987,104 | B2 | 1/2006 | Jacobs et al. |
| 7,148,242 | B2 | 12/2006 | Jacobs et al. |
| 2005/0261504 | A1 | 11/2005 | Kapa et al. |
| 2005/0277683 | A1 | 12/2005 | Jacobs et al. |
| 2007/0060753 | A1 | 3/2007 | Slade et al. |
| 2007/0135353 | A1 | 6/2007 | Slade et al. |
| 2007/0179298 | A1 | 8/2007 | Prashad et al. |

FOREIGN PATENT DOCUMENTS

WO    02/102790    12/2002

*Primary Examiner*—Kamal Saeed
*Assistant Examiner*—Sun Jae Y Loewe
(74) *Attorney, Agent, or Firm*—Lahive & Cockfield LLP; Elizabeth A. Hanley; Brian C. Trinque

(57) ABSTRACT

Improved processes for preparing intermediates useful for preparing antibacterial N-[1-oxo-2-alkyl-3-(N-hydroxyformamido)-propyl}-(carbonylamino-aryl or -heteroaryl)-azacyclo4-7alkanes or thiazacyclo4-7alkanes, which have one or more of the following features: (1) make use of a particular β-lactam intermediate; (2) which make use of a particular resolving agents, enantiomerically pure substituted propionic acids, especially (R)-2-butyl-3-hydroxy-propionic acid; (3) which avoid the use of hydrogen peroxide; and (4) which facilitate selective debenzylation reducing production of waste by-products.

6 Claims, No Drawings

CHEMICAL PROCESS FOR THE PREPARATION OF INTERMEDIATES TO OBTAIN N-FORMYL HYDROXY-LAMINE COMPOUNDS

This application claims benefit of U.S. Provisional Application No. 60/449,015, filed Feb. 21, 2003; U.S. Provisional Application No. 60/449,016, filed Feb. 21, 2003; and U.S. Provisional Application No. 60/449,01 7, filed Feb. 21, 2003, which in their entirety are herein incorporated by reference.

FIELD OF INVENTION

This invention is directed to a process for preparing certain antibacterial N-formyl hydroxylamine compounds.

BACKGROUND OF THE INVENTION

PDF is a metallopeptidase found in prokaryotic organisms, such as bacteria. Protein synthesis in prokaryotic organisms begins with N-formyl methionine (fMet). After initiation of protein synthesis, the formyl group is removed by the enzyme PDF; this activity is essential for maturation of proteins. It has been shown that PDF is required for bacterial growth. See Chang et al., *J. Bacteriol.*, Vol. 171, pp. 4071-4072 (1989); Meinnel et al., *J. Bacteriol.*, Vol. 176, No. 23, pp. 7387-7390 (1994); and Mazel et al., *EMBO J.*, Vol. 13, No. 4, pp. 914-923 (1994). Since protein synthesis in eukaryotic organisms does not depend on fMet for initiation, agents that will inhibit PDF are attractive candidates for development of new anti-microbial and anti-bacterial drugs.

Co-pending application Ser. No. 10/171,706, filed Jun. 14, 2002 (incorporated herein by reference in its entirety), PCT equivalent published as WO 02/102790 A1, discloses novel N-formyl hydroxylamine compounds that inhibit PDF and are therefore useful as antibacterial agents. The compounds disclosed therein are certain N-[1-oxo-2-alkyl-3-(N-hydroxyformamido)-propyl}(carbonylamino-aryl or -heteroaryl)-azacyclo4-7alkanes or thiazacyclo4-7alkanes, which are described in more detail hereinafter. Additionally, PCT application WO 99/39704 discloses other N-formyl hydroxylamine derivatives that are antibacterial agents by virtue of their PDF inhibiting capabilities. Improved processes have been discovered for preparing intermediates useful for preparing these N-[1-oxo-2-alkyl-3-(N-hydroxyformamido)-propyl}(carbonylamino-aryl or -heteroaryl)-azacyclo4-7alkanes or thiazacyclo4-7alkanes, which have one or more of the following features: (1) make use of a particular β-lactam intermediate; (2) which make use of particular resolving agents, e.g., enantiomerically pure substituted propionic acids, especially (R)-2-butyl-3-hydroxy-propionic acid; (3) which avoid the use of hydrogen peroxide (the use of hydrogen peroxide can be a safety concern because of its instability, therefore, this aspect of the invention is safer than the prior art process); and (4) which facilitate selective debenzylation, reducing production of waste by-products.

SUMMARY OF THE INVENTION

The present invention is directed to the novel processes for preparing certain intermediates which are useful to prepare certain N-formyl hydroxylamine compounds which are useful for inhibiting bacteria.

More specifically, the present invention is directed to a process for preparing a compound of formula (IX)

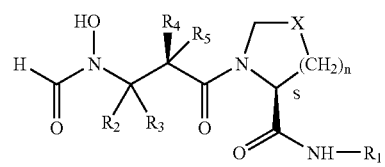

comprising Step A:
Contacting a compound of formula (I)

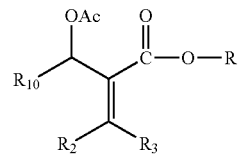

with a compound of the formula (II)

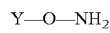

in a suitable solvent under conditions suitable to form a compound of the formula (III)

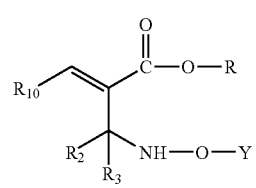

followed by asymmetric hydrogenation Step B:
Contacting the compound of formula (III) with hydrogen in the presence of a chiral ligand and a catalytic amount of a hydrogenation catalyst in a suitable solvent and under conditions suitable to form a compound of the formula (IV)

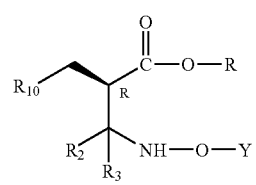

followed by Step C:
Contacting the compound of formula (IV) with a base such as a Grignard reagent in a suitable solvent under conditions suitable to form a compound of the formula (V)

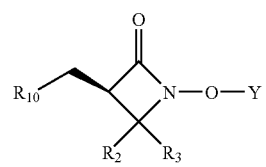

followed by Step D:

Contacting the compound of formula (V) with a compound of the formula (VI)

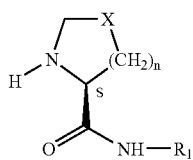
(VI)

in a suitable solvent, optionally in the presence of an activator under conditions suitable to form a compound of the formula (VII)

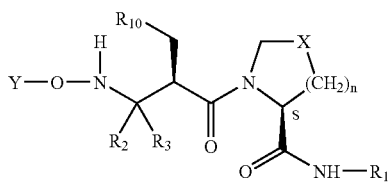
(VII)

followed by Step E:

Contacting the compound of formula (VII) with a formylating agent in a suitable solvent under conditions suitable to form the compound of formula (VIII):

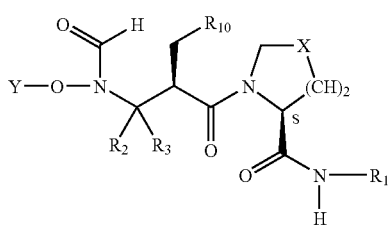
(VIII)

followed by Step F:

Converting the compound of formula (VIII) to the compound of formula (IX) by removing the hydroxy-protecting group using conventional hydrogenation techniques known in the art, e.g., by contacting the compound of formula (VIII) with hydrogen in the presence of a palladium catalyst, such as Pd/BaSO4, to form the compound of formula (IX)

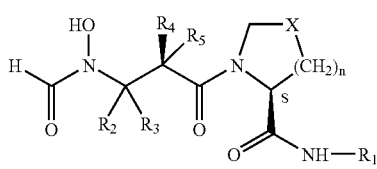
(IX)

wherein

X is —$CH_2$—, —S—, —CH(OH)—, —CH(OR)—, —CH(SH)—, —CH(SR)—, —$CF_2$—, —C=N(OR)— or —CH(F)—;

Y is a hydroxyl-protecting group such as benzyl;

R is alkyl;

Ac is acetyl;

each of $R_2$, $R_3$, $R_4$, $R_5$, and $R_{10}$ and independently is hydrogen or alkyl, or ($R_2$ or $R_3$) collectively form a $C_4$-$C_7$cycloalkyl R' is alkyl or aryl; and n is 0-3, provided that when n is 0, X is —$CH_2$—.

Furthermore, the present invention discloses process for preparing a compound of formula (IX) making use of enantiomerically pure substituted propionic acids, especially (R)-2-butyl-3-hydroxy-propionic acid More specifically, the present invention is directed to a process for preparing a compound of the formula (X)

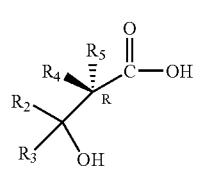
(X)

comprising Step 1:

Resolution of a racemate of the compound of the formula (X), i.e., a compound of formula (XI):

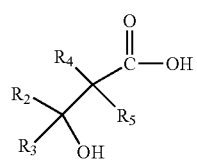
(XI)

by contacting the compound of formula (XI) with (R)-α-methylbenzylamine in a suitable solvent to form a (R,R)-diasteromeric salt of formula (XII)

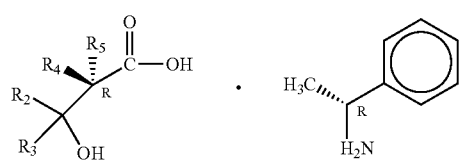
(XII)

followed by Step 2:

Contacting the compound of formula (XII) with a biphasic mixture of an aqueous mineral acid and an organic solvent to form the compound of formula (XI), wherein each of $R_2$, $R_3$, $R_4$ and $R_5$ is, independently, hydrogen or alkyl; or $R_2$ and $R_3$, collectively, form a $C_4$-$C_7$cycloalkyl, provided that $R_4$ and $R_5$ are different.

In addition, the present invention discloses process for preparing a compound of formula (IX) making use of a two-step process for preparing a compound of formula (XIII)

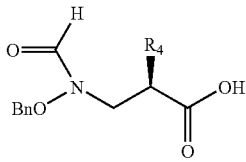

comprising Step i:
Contacting a compound of the formula (XIV)

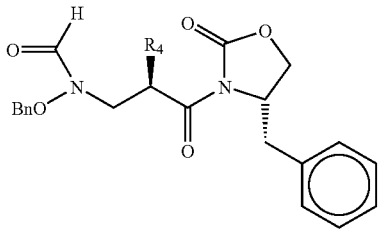

with an alkoxide of p-methoxybenzyl alcohol, in a suitable solvent under conditions to form a compound of formula (XV)

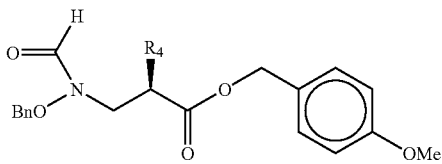

followed by deprotection Step ii:
Contacting the compound of formula (XV) with a strong organic acid in a suitable solvent under conditions to form the compound of formula (XIII), wherein
$R_4$ is alkyl;
Bn is benzyl; and
Me is methyl.

The present invention also provides a process for selectively converting the compound of formula (VIII) to the compound of formula (IX) by removing the hydroxy-protecting group, preferably benzyl, by contacting the compound of formula (VIII) with molecular hydrogen at sub-atmospheric pressures in the presence of a palladium catalyst in ethanol to form the compound of formula (IX).

Another aspect of the present invention is directed to a process for converting the compound of formula (XXV) to a compound of formula (XXVI) by removing hydroxyl-protecting group, preferably benzyl, by contacting the compound of formula (XXV) with a hydrogen transfer reagent comprising 4-methylmorpholine and formic acid in the presence of a palladium catalyst.

In addition to the above processes comprising multiple steps, e.g. Steps A-F, Steps 1-8, Steps i-ii, the present invention is directed to each of the steps individually, and to any two or more sequential steps.

DETAILED DESCRIPTION OF THE INVENTION

In particular, the present invention provides a process for preparing intermediates useful in the preparation of a N-[1-oxo-2-alkyl-3-(N-hydroxyformamido)propyl]-(carbonylamino-aryl or -heteroaryl)-azacyclo$_{4-7}$alkanes or thiazacyclo$_{4-7}$alkanes, e.g., a compound of formula (IX)

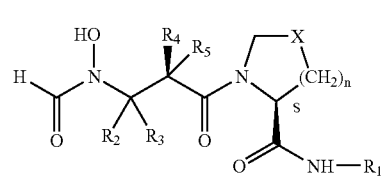

wherein $R_1$, $R_2$, $R_3$, $R_4$, $R_4$, X and n are as defined above.

To convert the compound of formula (VIII) to the compound of formula (IX) Step F can be performed wherein the hydroxyl-protecting group is removed using conventional hydrogenation techniques known in the art, e.g., by contacting the compound of formula (VIII) with hydrogen in the presence of a palladium catalyst, such as Pd/BaSO$_4$.

Preferred compounds discussed herein, e.g., of formula (IX), are disclosed in U.S. Ser. No. 10/171,706. For example, in the compounds described above, especially the compound of formula (IX), the following significances are preferred individually or in any sub-combination:

1. $R_1$ is a heteroaryl of formula (II.1)

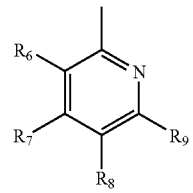

wherein
$R_6$, $R_7$ and $R_8$ are hydrogen; and
$R_8$ is methyl or trifluoromethyl; or
$R_6$, $R_7$ and $R_8$ are hydrogen; and
$R_9$ is fluoro; or
$R_6$, $R_8$ and $R_9$ are hydrogen; and
$R_7$ is ethyl or methoxy; or
$R_7$, $R_8$ and $R_9$ are hydrogen; and
$R_6$ is hydroxy; or
$R_7$ and $R_8$ are hydrogen;
$R_6$ is methoxy; and
$R_9$ is methyl; or
$R_1$ is a heteroaryl of formula (III.1)

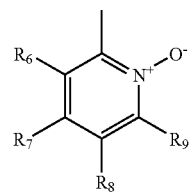

wherein
R_6, R_7 and R_9 are hydrogen; and
R_8 is fluoro or trifluoromethyl; or
R_6, R_8 and R_9 are hydrogen; and
R_7 is ethyl;
preferably R_1 is a heteroaryl of formula (II.1),
wherein
R_6, R_8 and R_9 are hydrogen; and
R_7 is ethyl
or R_1 is a heteroaryl of formula (III.1),
wherein
R_6, R_7 and R_9 are hydrogen; and
R_8 is fluoro.
2. X is —CH_2—, —CH(OH)—, —CH(OR)—, —CF_2— or —CH(F)—, preferably X is —CH_2—
3. R_2, R_3, R_5 are hydrogen;
4. R_4 and R_10 are alkyl, preferably $C_1$-$C_6$ alkyl for R_4, such as n-butyl, and $C_1$-$C_5$ alkyl for R_10 such as n-propyl;
5. n is 1.

Unless otherwise stated, the following terms as used in the specification have the following meaning.

The term "alkyl" refers to saturated aliphatic groups, including cycloalkyl or substituted alkyl, preferably straight-chain, branched-chain and cyclic groups having from 1-10 carbons atoms. More preferably, "alkyl" or "alk", whenever it occurs, is a $C_1$-$C_7$alkyl, particularly, $C_{1-4}$alkyl. Examples of "alkyl" or "alk" include, but are not limited to, methyl, ethyl, n-propyl, isopropyl, n-butyl, isobutyl, sec-butyl, t-butyl, n-pentyl, neopentyl, n-hexyl or n-heptyl, cyclopropyl and especially n-butyl.

The term "cycloalkane" or "cycloalkyl" contains from 3- to 7-ring carbon atoms, and is, e.g., cyclopropyl, cyclobutyl, cyclopentyl and cyclohexyl.

The term "aryl" or "Ar" refers to an aromatic carbocyclic group of 6-14 carbon atoms having a single ring including, but not limited to, groups, such as phenyl; or multiple condensed rings including, but not limited to, groups, such as naphthyl or anthryl; and, is especially, phenyl.

The term "heteroaryl" or "HetAr" refers to a 4- to 7-membered, monocyclic aromatic heterocycle or a bicycle that is composed of a 4- to 7-membered, monocylic aromatic heterocycle and a fused-on benzene ring. The heteroaryl has at least one hetero atom, preferably one or two heteroatoms including, but not limited to, heteroatoms, such as N, O and S, within the ring. A preferred heteroaryl group is pyridinyl, pyrimidinyl or benzdioxolanyl.

The aryl or heteroaryl may be substituted or unsubstituted by one or more substituents including, but not limited to, $C_1$-$C_7$alkyl, particularly, $C_1$-$C_4$alkyl, such as methyl, hydroxy, alkoxy, acyl, acyloxy, SCN, halogen, cyano, nitro, thioalkoxy, phenyl, heteroalkylaryl, alkylsulfonyl and formyl.

The term "heteroalkyl" refers to saturated or unsaturated $C_1$-$C_{10}$alkyl as defined above and, especially, $C_1$-$C_4$heteroalkyl which contain one or more heteroatoms, as part of the main, branched or cyclic chains in the group. Heteroatoms may independently be selected from the group consisting of —NR—, where R is hydrogen or alkyl, —S—, —O— and —P—; preferably —NR—, where R is hydrogen or alkyl; and/or —O—. Heteroalkyl groups may be attached to the remainder of the molecule either at a heteroatom (if a valence is available) or at a carbon atom. Examples of heteroalkyl groups include, but are not limited to, groups, such as —O—CH_3, —CH_2—O—CH_3, —CH_2—CH_2—O—CH_3, —S—CH_2—CH_2—CH_3, —CH_2—CH(CH_3)—S—CH_3 and —CH_2—CH_2—NH—CH_2—CH_2—.

The term "alkoxy", as used herein, refers to a $C_1$-$C_{10}$alkyl linked to an oxygen atom, or preferably, $C_1$-$C_7$alkoxy, more preferably, $C_1$-$C_4$alkoxy. Examples of alkoxy groups include, but are not limited to, groups such as methoxy, ethoxy, n-butoxy, tert-butoxy and allyloxy.

The term "acyl", as used herein, refers to the group —(O)CR, where R is alkyl, especially, $C_1$-$C_7$alkyl, such as methyl. Examples of acyl groups include, but are not limited to, acetyl, propanoyl and butanoyl.

The term "acyloxy", as used herein, refers to the group —OC(O)R, wherein R is hydrogen, alkyl, especially, $C_1$-$C_7$alkyl, such as methyl or ethyl, or phenyl or substituted alkyl as defined above.

The term "alkoxycarbonyl", as used herein, refers to the group —COOR, wherein R is alkyl, especially, $C_1$-$C_7$alkyl, such as methyl or ethyl.

The term "halogen" or "halo" as used herein, refers to chlorine, bromine, fluorine, iodine and, is especially, fluorine.

The term "thioalkoxy", as used herein, means a group —SR, where R is an alkyl as defined above, e.g., methylthio, ethylthio, propylthio, butylthio and the like.

The term "heteroalkylaryl", as used herein, means a heteroalkyl group, e.g., —O—CH_2— substituted with an aryl group, especially, phenyl. The phenyl group itself may also be substituted with one or more substituents, such as halogen, especially fluoro and chloro; and alkoxy, such as methoxy.

The term "alkylsulfonyl", as used herein, means a group —SO_2R, wherein R is alkyl, especially, $C_1$-$C_7$alkyl, such as methyl sulfonyl.

The term "enantiomericly pure" or "optically pure" means that the enantiomeric purity is greater than 55%, preferably greater than 80%, more preferably greater than 90%, and most preferably greater than 95%.

To prepare the compounds of formula (I), a compound of the formula

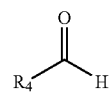

is contacted with a compound of the formula

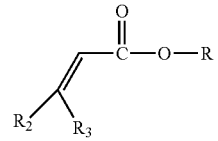

in the presence of a catalytic amount of a catalyst, such as DABCO, DBU or DBN under sufficient conditions to form a compound of the formula

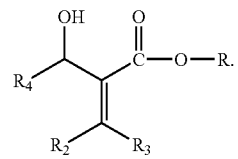

The above reaction is a Baylis-Hillman reaction.

The compound thus formed can then be reacted with acetic anhydride in a suitable solvent, in the presence of a base, such as 4-DMAP or a trialkylamine, e.g., triethylamine or tripropylamine, to form the compound of formula (I).

Preferably $R_2$ and $R_3$ are hydrogen and $R_4$ is n-propyl; which results in a compound such as formula (Ic)

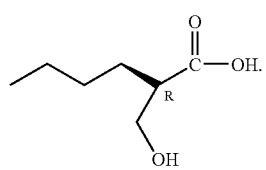

(Ic)

The solvent used for the various steps A-F are typically organic solvents, although in some situations, aqueous/organic solvents can be used. Examples of suitable solvents include dioxane, methylene chloride, dichloromethane, toluene, acetone, methylethylketone, THF, isopropyl acetate, DMF, alcohols, especially higher-branched alcohols, such as t-butanol and the like.

For Step A, a typical temperature is about 10° C. to about 50° C., preferably about 20° C. to about 25° C. The solvent for Step A is typically THF, DMF, NMP and the like.

For asymmetric hydrogenation Step B, a typical temperature is about 10° C. to about 50° C., preferably about 20° C. to about 25° C. The solvent for Step B is not known to be critical and can be a wide variety of solvents, such as dioxane, methylene chloride, dichloromethane, toluene, acetone, methylethylketone, THF, isopropyl acetate, DMF, alcohols, especially higher-branched alcohols, such as t-butanol and the like. The hydrogen for Step is typically in the form of hydrogen gas and the Step B is typically preformed above atmospheric pressure, e.g., at about 40 psi to about 100 psi, more typically at about 45 psi to about 55 psi. The chiral ligand for Step B can be (2S,5S)-Me-Duphos, (1R,1'R,2S,2'S)-TangPhos and the like. (1R,1'R,2S,2'S)-TangPhos has the formula

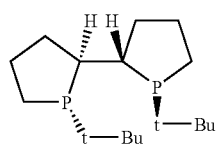

(XVI)

The amount of Chiral ligand is typically about 1 mole % to about 15 mole % relative to the substrate. The hydrogenation catalyst is preferably homogenous. The hydrogenation catalyst is preferably a transition metal complex. Typical transition metal catalysts contain rhodium (Rh I) or ruthenium (Ru II). A preferred catalyst is bis(norbomadiene)rhodium(I) tetrafluoroborate. The amount of catalyst is a catalytic amount, typically about 1 mole % to about 5 mole % relative to the substrate.

For cyclization Step C, a typical temperature is about −10° C. to about 20° C., preferably about 0° C. The pH for Step C is basic, typically, about 8 pH to about 12 pH. The Grignard reagent used in Step C can be any suitable organomagnesium compound known in the art, such as methylmagnesium chloride, ethylmagnesium chloride, isopropyl magnesium chloride, n-butylmagnesium chloride, methylmagnesium bromide, isopropylmagnesium bromide, cyclopropylmagnesium bromide, ethylmagnesium iodide and the like. The amount of Grignard reagent employed is a de-protonating amount which is typically in molar excess to the amount of formula (IV), e.g., about 1-5 equivalents relative to formula (IV). A preferred solvent is acetone or methylethylketone.

For Step D, a typical temperature is about 30° C. to about 150° C., preferably about 60° C. to about 80° C. The pH for Step D is typically about 5 pH to about 11 pH. The activator for Step D is a compound which protonates the β-lactam keto oxygen; such activators include, e.g., mild (weak) organic acids, such as branched or unbranched carboxylic acids, e.g., 2-ethylhexanoic acid, acetic acid, isobutryic acid and the like. If an aqueous alcoholic solvent is used an activator is not needed; preferred aqueous alcoholic solvents include MeOH.H$_2$O, EtOH.H$_2$O and the like. If an activator is used a preferred solvent is THF, dioxane or dimethoxyethane. If an activator is used it is used in an protonating amount which is typically about 0.1 molar equivalents to about 2 molar equivalents relative to formula (V).

For Step E, a typical temperature is about −30° C. to about 50° C., preferably about 0° C. to about 25° C. The pH for Step E is not critical and can vary considerably. For Step E the solvent should not be an alcoholic solvent. The formylating agent can be, e.g., HCO$_2$H/Ac$_2$O, trifluoroethylformate and the like, and is present in a formylating amount which is typically about 1 molar equivalent to about 2 molar equivalents relative to formula (VII). A preferred solvent is EtOAc, isopropylacetate, t-butylacetate or THF.

To prepared the S enantiomer instead of the R enantiomer of the compounds prepared herein, the appropriate isomer of the chiral ligand will be used, e.g., (2R,5R)-Me-Duphos and (1S1'S,2R,2'R)-TangPhos. For example, Step B will comprise:

Contacting a compound of the formula (III)

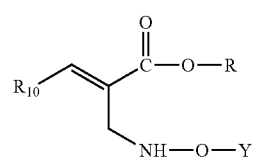

(III)

with hydrogen in the presence of a chiral ligand and a catalytic amount of a hydrogenation catalyst in a suitable solvent and under conditions suitable to form a compound of the formula (IV')

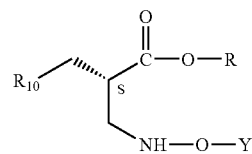

(IV')

All of the other steps will be the same.

Insofar as the production of starting materials is not particularly described, the compounds are known or may be prepared analogously to methods known in the art or as disclosed in the examples hereinafter.

It is further preferred that in the optically pure compound of formula (X) that $R_2$, $R_3$ and $R_5$ are hydrogen and that $R_4$ is alkyl; such a compound has the formula (Xa)

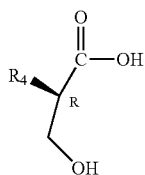
(Xa)

Preferably in formula (X), $R_4$ is n-butyl, where such compound has the formula (Xb)

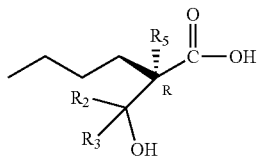
(Xb)

It is even more preferred that $R_2$, $R_3$ and $R_5$ are hydrogen and that $R_4$ is n-butyl where such compound has the structure (Xc):

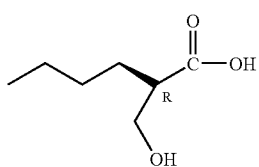
(Xc)

To prepare the starting material of the above-described process, i.e., formula (XI) the corresponding alkyl ester can be hydrolyzed as described by Stetter and Kuhlmann, *Synthesis*, pp. 29-30 (1979).

For example, in a preferred preparation, a compound of formula (XVII)

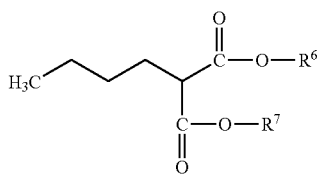
(XVII)

is contacted with a strong base, such as KOH, to form a compound of formula (XVIII)

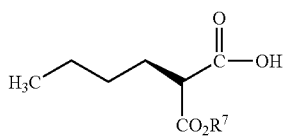
(XVIII)

followed by contacting the compound of formula (XVIIII) with a reducing agent, such as $LiBH_4$, $NaBH_4$ or borane in a suitable solvent, such as THF, DMF or diethyl ether, to form a starting material for the present process, e.g., a compound of formula (IXa)

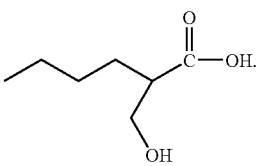
(IXa)

Following the first step (Step 1), it is preferred to re-crystallize the diasteriomeric salt from a suitable solvent, preferably from the same solvent system, prior to performing the second step (step 2).

A preferred process of the invention comprises resolution of a compound of formula (IXa) by contacting said compound with (R)-α-methylbenzylamine in a mixture of ethyl acetate and 2-propanol to form a compound of formula (IIIa)

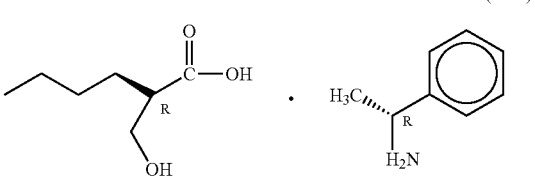
(XIIa)

followed by re-crystallization of the diasteriomeric salt, i.e., the compound of formula (IIIa), from the same solvent, followed by contacting the compound of formula (XIIa) with a mixture of HCl (preferably about 2 N), and isopropyl acetate to form the compound of formula (Xc)

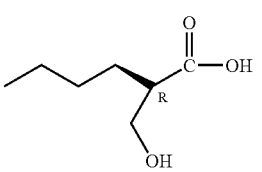
(Xc)

To form the active antibacterial agents, a third step (Step 3) is performed wherein the compound formed by the second step, i.e., the compound of formula (X), is contacted with a compound of the formula (XIX)

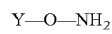
(XIX)

in the presence of a carboxy-activating agent, in a suitable solvent under conditions suitable to form a compound of the formula (XX)

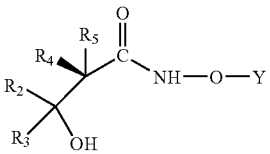
(XX)

followed by Step 4:

Contacting a formula (XX) with a compound of the formula (XXI)

(XXI)

wherein R' is alkyl or aryl and X' is halo, in the presence of a base in a suitable solvent, under conditions suitable to form a compound of the formula (XXII)

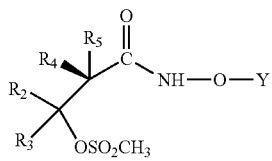

(XXII)

followed by Step 5:
Contacting a formula (XXII) with a base in a suitable solvent under conditions suitable to form a compound of the formula (XXIII)

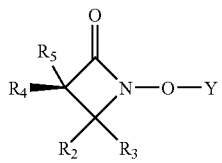

(XXIII)

followed by Step 6:
Contacting a formula (XXIII) with a compound of the formula (VI)

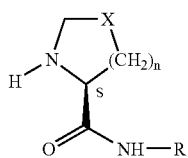

(VI)

in a suitable solvent optionally in the presence of an activator under conditions suitable to form a compound of the formula (XXIV)

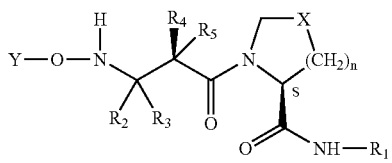

(XXIV)

followed by Step 7:
Contacting a formula (XXIV) with a formylating agent in a suitable solvent under conditions suitable to form compound (XXV):

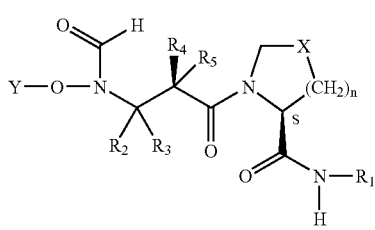

(XXV)

followed by Step 8:
converting the compound of formula (XXIV) to the compound of formula (IX) by removing the hydroxy-protecting group using conventional hydrogenation techniques known in the art, e.g., by contacting the compound of formula (XXIV) with hydrogen in the presence of a palladium catalyst, such as Pd/BaSO$_4$, to form the compound of formula (IX)

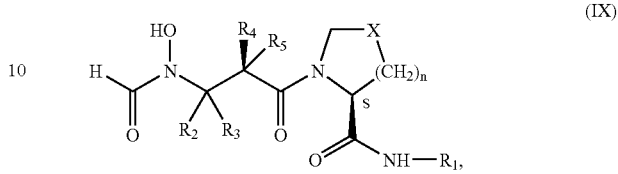

(IX)

If desired, the (S) enantiomer can be prepared instead of the (R) enantiomer by using the (S) form of the resolving agent rather than the (R) form. Such a process comprises preparing a compound of the formula (X')

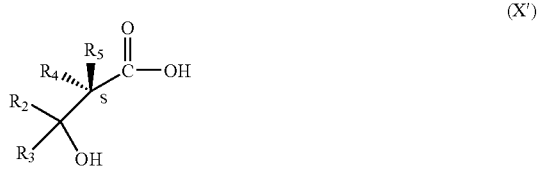

(X')

comprising Step 1':
Resolution a racemate of the compound of the formula (X'), i.e., a compound of formula (XI):

(XI)

by contacting the compound of formula (X') with (S)-α-methylbenzylamine in a suitable solvent to form a (S,S)-diasteromeric salt of formula (III')

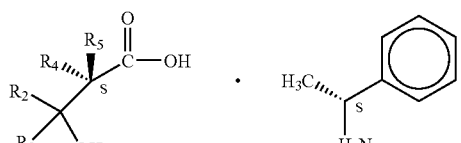

followed by Step 2':
Contacting the compound of formula (XII') with a biphasic mixture of an aqueous mineral acid and an organic solvent to form the compound of formula (X'). The active (S) antibacterial agents can then be prepared using Steps 3-8 as described above.

Pressure is not known to be critical for carrying out the various steps 1-8 and 1'-2' of the invention. Generally, depending on the particular step, a temperature of about −10° C. to about 150° C., preferably about 0° C. to about 80° C., is typically employed. Typically about atmospheric pressure is used for convenience; however, variations to atmospheric pressure are not known to be detrimental. Oxygen is not known to be detrimental to the process, therefore for convenience, the various steps can be performed under ambient air, although an inert atmosphere, such as nitrogen or argon, can be used if desired. For convenience, equimolar amounts of reactants are typically used; however, molar ratios can vary from about 1-2 equivalents, relative to the other reactant. The pH for most steps is typically about 2 pH to about 12 pH, although, as mentioned below, the pH for Step 2 must be very acidic. The solvent to be used for the various steps will depend on the nature of the reactants and other conditions and can be, e.g., ethyl acetate, isopropyl acetate, toluene, dichloromethane dioxane, methylene chloride, toluene, acetone, methylethylketone, THF, DMF, alcohols and the like; however, the solvents for Steps 1 and 2 are listed below.

For Step 1, a typical temperature is about 10° C. to about 90° C. Preferably in Step 1, the reaction mixture is initially heated to about 50° C. to about 90° C., and then cooled to crystallize the desired compound, e.g., at a temperature of about 10° C. to about 40° C. The amount of resolving agent, i.e., (R)-α-methylbenzylamine, employed is typically about 0.7 molar equivalents to about 1.5 molar equivalents relative to formula (XI). The solvent for Step 1 is a mixture of an ester or an alkyl nitrile and an alcohol. Examples of esters include, e.g., alkyl acetates, such as isopropyl acetate, t-butyl acetate, ethyl acetate and the like. Examples of alkyl nitriles include, e.g., acetonitrile and the like. Examples of alcohols include methanol, ethanol, isopropanol and the like. The ratio of ester or alkyl nitrile to alcohol can vary from about 90:10 to about 10:90, preferably about 75:25 to about 25:75, and most preferably about 50:50, the preceding ratios being based on volume:volume. The most preferred solvent is a mixture of ethyl acetate:2-propanol (50:50, vol:vol).

For Step 2, a typical temperature is about 10° C. to about 30° C., preferably about 20° C. to about 25° C. Due to the presence of the acid, the pH for Step 2 is acidic and is typically about a pH of 1 or less. The solvent for step 2 is a mixture of an aqueous mineral acid and an organic solvent which forms a biphasic solvent comprising and aqueous and organic phases. The ratio (volume:volume) of aqueous mineral acid: organic solvent can vary widely, e.g., 90:10-10:90, more typically 60:40-40:60. The desired compound of formula (X) can be recovered from the organic phase using conventional purification and/or separation techniques known in the art such as distillation, filtration and the like. To increase yield, multiple extractions from the aqueous phase can be performed with the organic layers combined and then washed with an aqueous inorganic salt solution, such as a 10-40% by weight aqueous solution of sodium chloride. Strong mineral acids are typically used for Step 2, e.g., HCl, $H_2SO_4$ and the like. The strength of the acid is strong enough for forming the desired compound, typically about 1 N to about 6 N, with about 2 N being preferred. The organic solvent can be ethyl acetate, isopropyl acetate, toluene, dichloromethane dioxane, methylene chloride, toluene, acetone, methylethylketone, THF, DMF and the like.

In U.S. Ser. No. 10/171,706, General Procedure A describes forming the compound of formula (XIII) by treatment of the compound of formula (XIV) with LiOH and $H_2O_2$. Another aspect of present process eliminates the need for using $H_2O_2$, thereby resulting in a process that is much safer, particularly upon scale-up.

In Step i, the alkoxide of p-methoxybenzyl alcohol can be formed in situ by contacting p-methoxybenzyl alcohol with an organic base such as LiHMDS, NaHMDS, and the like. The solvent for Step i can be, for example, diethyl ether, DMF, NMP, THF and the like. The temperature for Step i is not known to be critical and can vary from about 10° C. to about 40° C. and, for convenience, is typically preferred at RT, e.g., about 20° C. to about 25° C.

For Step ii, the strong organic acid can be formic acid, p-toluenesulfonic acid, and the like. The acid typically solubilizes the compound of formula (XV), and therefore serves as the solvent for the reaction. The amount of acid is, therefore sufficient to solubilize and deprotect the compound of formula (XV). The temperature for Step ii is not known to be critical and can vary from about 10° C. to about 40° C. and, for convenience, is typically preferred at RT, e.g., about 20° C. to about 25° C.

For both Steps i and ii, the desired products can be purified and concentrated using conventional techniques known in the art. For example, a mixture of ethyl acetate and aqueous acid or base can be added to the reaction mixture to form a biphasic solution wherein the desired product will be in the organic phase. After separation of the organic phase, it can, if desired, be subject to multiple extractions with the same or different solutions. Typical acids for this use are strong mineral acids such as HCl, $H_2SO_4$, and the like, and typical bases are sodium carbonate, and the like. Removal of the solvent can be accomplished using conventional techniques, e.g., distillation under reduced pressure. Further purification of the desired product can also be preformed, e.g., using chromatography such as flash chromatography, HPLC, and the like.

Compounds of formula (XIII) can be converted to active anti-bacterial compounds of formula (IX), by contacting the compounds of formula (XIII) with a compound of formula (VI')

(VI')

in the presence of hydrogen gas and a palladium on carbon catalyst in a suitable solvent to form a compound of formula (XXVII)

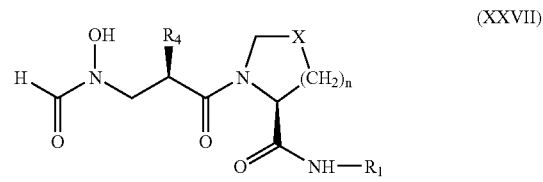

(XXVII)

Insofar as the production of starting materials is not particularly described, the compounds are known or may be prepared analogously to methods known in the art or as disclosed in the examples hereinafter. In U.S. Ser. No. 10/171, 706, General Procedure A describes forming the compound of formula XXVII.

Furthermore, another aspect of the present invention provides a novel process for preparing active anti-bacterial compounds of formula (IX) by treatment the compounds of formula (VIII) with hydrogen at sub-atmospheric partial pressures in the presence of a palladium catalyst in ethanol. The present process minimizes production of by-product, thereby resulting in a process that is environmentally benign. The reaction may be carried out by sparging a gaseous mixture of hydrogen and nitrogen at 1 atm total pressure in a reaction mixture containing compound of formula (VIII), ethanol and a palladium catalyst, e.g., palladium on carbon. The desired hydrogen partial pressure is attained by varying the relative flow rate of nitrogen and hydrogen. A reasonable reaction time is required, i.e., the reaction is allowed to proceed until the desired product is formed.

More specifically, another aspect of the present invention is directed to a process for preparing a compound of formula (IX)

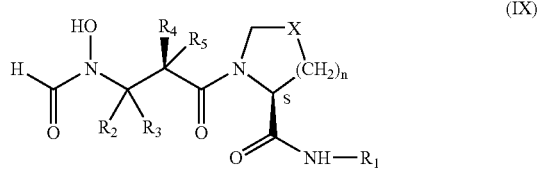

(IX)

wherein
X is —$CH_2$—, —S—, —CH(OH)—, —CH(OR)—, —CH(SH)—, —CH(SR)—, —$CF_2$—, —C=N(OR)— or —CH(F)—;
$R_1$ is aryl or heteroaryl, preferably

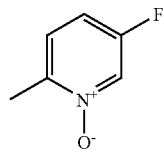

each of $R_2$, $R_3$, $R_4$ and $R_5$ independently is hydrogen or alkyl, or ($R_2$ or $R_3$) collectively form a $C_4$-$C_7$cycloalkyl, preferably $R_2$, $R_3$, $R_5$ are hydrogen and $R_4$ is n-butyl;
n is 0-3, preferably 1.

Comprising a step:
Converting the compound of formula (XXV)

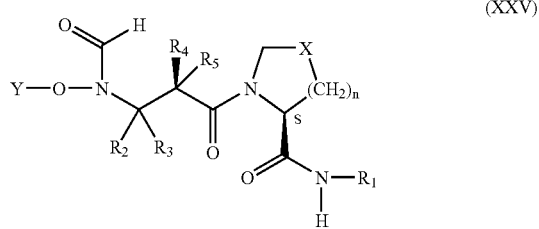

(XXV)

wherein
Y is a hydroxy-protecting group, preferably benzyl, to the compound of formula (IX) by removing the hydroxyl-protecting group by contacting the compound of formula (XXV) with molecular hydrogen at hydrogen partial pressures below 1 atm, preferably about 0.1 atm to about 0.24 atm, while maintaining a total pressure of about 1 atm in the presence of a palladium catalyst, such as 5% Pd/C, in a suitable solvent, preferably ethanol, at about 10 to about 30° C., typically about 20° C.

When the debenzylation with molecular hydrogen is carried out at typical conditions (e.g., hydrogen partial pressures≧1 atm) hydrogenolysis of the N—O bond in the pyridine N-oxide moiety occurs to a significant extent (i.e. yields>1%), resulting in production of a by-product (designated as "des-oxy C10") in substantial amounts.

Because des-oxy C10 is difficult to separate from the reaction mixture by crystallization, it is highly desirable to eliminate or at least limit its production to very small amounts.

A means has been found to conduct the debenzylation very selectively, i.e., with des-oxy C10 yields of under 1%, by performing the reaction at hydrogen partial pressures below 1 atm. The examples 14 and 15 describe the experimental methods and results in detail.

Another aspect of the present invention is selective O-debenzylation in the presence of pyridine N-oxides via hydrogen transfer using formic acid/4-methylmorpholine.

The penultimate step of a synthesis of the compound of formula (IX) comprises a catalytic removal of hydroxy-protecting group by contacting the compound of formula (XXV) with hydrogen in the presence of a catalyst such as Pd/C. The compound of formula (XXV) may include a pyridine N-oxide group; when the removal of hydroxy-protecting group is carried out at typical conditions (e.g., hydrogen partial pressures at or above 1 atm) hydrogenolysis of the N—O bond in the pyridine N-oxide occurs to a significant extent, resulting in production of by product in significant amounts. The latter is difficult to separate.

The deprotection can be carried out selectively via hydrogen transfer instead of using molecular hydrogen. A means has been found to conduct deprotection very selectively with a hydrogen transfer reagent comprising 4-methylmorpholine and formic acid. Preferably 1.6 eq of 4-methylmorpholine and 1.4 eq of formic acid in the presence of a catalyst. Such chemical transformatin occurs at elevated temperatures, preferably reaction mixture is being heated at about 45° C. for about 25±10 min.

The following abbreviations are used:
HPLC=high performance liquid chromatography
Ac=acetyl
Fmoc=9-fluorenylmethyl-oxycarbonyl
Mom=methoxy methyl ether
Mem=methoxy ethoxy methyl ether
NPEOC=4-nitrophenethyloxycarbonyl
NPEOM=4-nitrophenethyloxy-methyloxycarbonyl The following abbreviations are used:

| | |
|---|---|
| DMAP = dimethylamino-pyridine | Ph = phenyl |
| DMF = dimethylformamide | NMP = N-methylpryrrolidone |
| EtOAc = ethyl acetate | DABCO = 1,4-diazabicyclo[2.2.2]octane |
| EtOH = ethanol | psi = pounds per square inch |
| HPLC = high performance liquid chromatography | TBDMS = t-butyldimethylsilyl |
| | TMSCl = trimethylsilyl chloride |
| Me = methyl | aq. = aqueous |
| MeOH = methanol | Et = ethyl |
| RT = room temperature | iPr = isopropyl |
| THF = tetrahydrofuran | Bn = benzyl |
| Nvom = nitroveratryl oxy-methyl ether | DABCO = 1,4-diazabicyclo[2.2.2]octane |

The following examples are to illustrate the invention but should not be interpreted as a limitation thereon.

EXAMPLE 1

3-Hydroxy-2-methylenehexanoic acid methyl ester

A mixture of butanol (72.11 g, 1,000 mmol), methyl acrylate (129.14 g, 1,500 mmol) and DABCO (22.44 g, 200 mmol) is allowed to react at room temperature under $N_2$ for 7 days. The reaction mixture is concentrated on Rotavap under reduced pressure (20 mbar) until no further solvent distills. The residue colorless liquid is dissolved in toluene (800 mL) and washed sequentially with 2 N HCl acid (250 mL), water (250 mL), saturated aq. sodium bicarbonate solution (120 mL) and water (150 mL). The toluene layer is concentrated on Rotavap under reduced pressure (20 mbar) until no further solvent distills to afford 3-hydroxy-2-methylenehexanoic acid methyl ester (96.7 g, yield: 61.1%) as a colorless liquid.

EXAMPLE 2

3-Acetoxy-2-methylenehexanoic acid methyl ester

A mixture of 3-hydroxy-2-methylenehexanoic acid methyl ester (55.37 g, 350 mmol) and DMAP (4.28 g, 35 mmol) in toluene (400 mL) is cooled to 0-5° C. and to it is added acetic anhydride (42.88 g, 420 mmol) dropwise in ~30 minutes while maintaining the temperature at 0-5° C. The resulting solution is allowed to warm to room temperature in 1 hour. After stirring for 3 hours at RT, the reaction mixture is cooled to 0-5° C. and to it is added 1 N HCl acid (80 mL), in 20 minutes. The organic layer is separated and washed sequentially with water (80 ml), saturated aqueous sodium bicarbonate solution (2×80 mL) and water (80 mL). The organic layer is concentrated on Rotavap under reduced pressure (20 mbar) until no further solvent distills to afford 3-acetoxy-2-methylenehexanoic acid methyl ester (68.39 g, yield: 97.5%) as a colorless liquid.

EXAMPLE 3

2-[[(Phenylmethoxy)amino]methyl]-2-hexenoic acid methyl ester

A mixture of 3-acetoxy-2-methylenehexanoic acid methyl ester (4.00 g, 20 mmol) and O-benzylhydroxylamine (7.39 g, 60 mmol) in THF (30 mL) is allowed to react at RT under $N_2$ for 2 days. The reaction mixture is concentrated on Rotavap under reduced pressure (20 mbar) until no further solvent distills. The residue liquid is dissolved in ethyl acetate (75 mL) and washed with saturated aqueous sodium bicarbonate solution (50 mL). The ethyl acetate layer is concentrated on Rotavap under reduced pressure (20 mbar) until no further solvent distills to afford a colorless liquid (11.2 g).

The crude material is chromatographed (silica gel, 5% ethyl acetate in heptane) to afford a ~1:1 mixture of (E) and (Z)-2-[[(phenylmethoxy)amino]methyl]-2-hexenoic acid methyl ester (4.01 g, yield: 76%) as a colorless liquid.

EXAMPLE 4

2-[[(Phenylmethoxy)amino]methyl]-(2S)-hexanoic acid methyl ester

A ~1:1 mixture of (E) and (Z)-2-[[(phenylmethoxy)amino]methyl]-2-hexenoic acid methyl ester (3.95 g, 15 mmol), bis(norbornadiene)rhodium(I)tetrafluoroborate (56.1 mg, 0.15 mmol) and (1S,1'S,2R,2'R)-TangPhos (47.3 mg, 0.165 mmol) in de-oxygenated methanol (90 mL) in a Parr bottle is hydrogenated under $H_2$ (45-55 psi) at RT for 24 hours. The reaction mixture is concentrated on Rotavap under reduced pressure (20 mbar) until no further solvent distills. The residue liquid is dissolved in a mixture of ethyl acetate/heptane (50/50, 10 mL) and filtered through a silica gel pad (~12 g). The silica gel pad is rinsed with a mixture of ethyl acetate/heptane (50/50, 200 mL). The filtrates are combined and concentrated on Rotavap under reduced pressure (20 mbar) until no further solvent distills to afford 2-[[(phenylmethoxy)amino]methyl]-(2S)-hexanoic acid methyl ester (3.76 g, yield: 94%, S:R=98.0:2.0) as a liquid.

2-[[(Phenylmethoxy)amino]methyl]-(2S)-hexanoic acid methyl is also prepared using (2R,5R)-Me-Duphos (yield: 95%, R:S=98:2).

EXAMPLE 5

2-[[(Phenylmethoxy)amino]methyl]-(2R)-hexanoic acid methyl ester (1R,1'R,2S,2'S)-TangPhos affords 2-[[(phenylmethoxy)amino]methyl]-(2R)-hexanoic acid methyl ester (yield: 96%, R:S=98.6:1.4)

Similarly, (2S,5S)-Me-Duphos affords 2-([(phenylmethoxy)amino]methyl]-(2R)-hexanoic acid methyl ester (yield: 98%, R:S=98.8:1.2).

EXAMPLE 6

1-Benzyloxy-(3S)-butyl-2-azitidinone

To a solution of 2-[[(phenylmethoxy)amino]methyl-(2S)-hexanoic acid methyl ester (265 mg, 1.0 mmol) in tetrahydrofuran (5.0 ml) at 0° C. is added dropwise, 3.0 M methylmagnesium chloride (0.76 mL, 2.30 mmol) at a rate maintaining the same internal temperature. The resulting solution is stirred for 1 hour at 0-3° C. and the reaction is quenched by addition of pH 7 phosphate buffer (5.0 ml). Ethyl acetate (30 mL) is added, the organic layer is separated and washed with water (20 mL). The organic layer is concentrated under reduced pressure to afford the crude product as an oil which is purified by flash chromatography on silica gel to give 1-benzyloxy-(3S)-butyl-2-azitidinone (112 mg, 50% yield, S:R=92.7:7.3)).

EXAMPLE 7

1-Benzyloxy-(3R)-butyl-2-azitidinone

2-[[(phenylmethoxy)amino]methyl-(2R)-hexanoic acid methyl ester affords 1-benzyloxy-(3R)-butyl-2-azitidinone.

The examples 8, 9, 10 and 11 that follow make reference to reaction scheme 1 below:

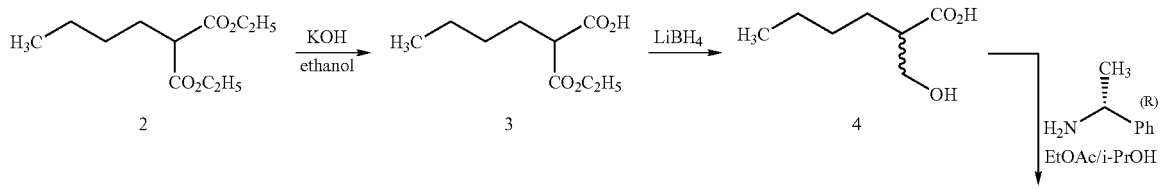

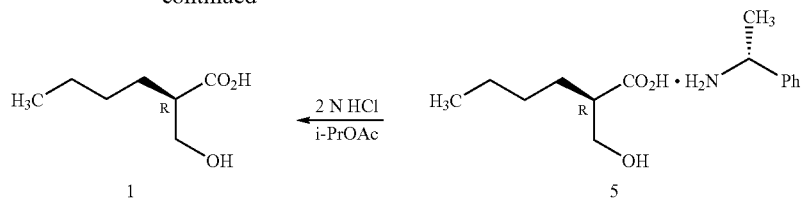

EXAMPLE 8

Preparation of (±)-2-butyl-3-hydroxypropionic acid (4)

A 12 L, 4-necked, round-bottomed flaks, equipped with a mechanical stirrer, digital thermometer, and nitrogen inlet-outlet is charged with 2-butyl-propanedioic acid monoethyl ester (3, 450.0 g, 2.39 mol) and isopropanol (4.5 L). The solution is cooled to an internal temperature at 15-18° C. and a 2 M solution of lithium borohydride (2.4 L, 4.8 mol) in tetrahydrofuran is added over a period of 1.5 hours while maintaining the internal temperature at 15-25° C. The stirring is continued for an additional 3 h. The reaction mixture is cooled to an internal temperature at 10-13° C. and quenched by the addition of 2 N HCl (2.4 L) over a period of 1 hour while maintaining the internal temperature at 10-25° C. The reaction mixture is concentrated at 35-40° C. (20 mbar) to collect ~7.5 L of the solvent to obtain a suspension (~1.9 kg). This suspension is diluted with water (2.0 L) and ethyl acetate (2.5 L) and the biphasic mixture is stirred for 1 hour. The organic layer is separated and the aqueous layer is extracted with ethyl acetate (2.0 L). The combined organic layers are washed with 20% aqueous solution of sodium chloride (1.0 L) and concentrated under vacuum (20 mbar) until no further solvent distills to afford crude (±)-2-butyl-3-hydroxypropionic acid (4, 349.4 g, 100%) as a colorless liquid, which is used as such in the next step.

EXAMPLE 9

Resolution of (±)-2-butyl-3-hydroxypropionic acid (4)

A 5 L, 4-necked, round-bottomed flaks, equipped with a mechanical stirrer, digital thermometer, reflux condenser, addition funnel with nitrogen inlet-outlet, and heating mantle is charged with (R)-α-methylbenzylamine (280.7 g, 2.316 mol), isopropanol (1.9 L) and ethyl acetate (1.63 L). The solution is stirred and heated to an internal temperature at 60-65° C., and a solution of (±)-2-butyl-3-hydroxypropionic acid (4, 322.5 g, 2.206 mol) in ethyl acetate (0.2 L) is added over a period of 15 min while maintaining the internal temperature at 60-70° C. The addition funnel is washed with ethyl acetate (0.2 L) and added to the mixture. The solution is cooled to 20-25° C. over a period of 2 hours and the resulting suspension is stirred at the same temperature for an additional 5 hours. The solids are collected by filtration, washed with a mixture of ethyl acetate-isopropanol (2:1 v/v) in two equal portions of 0.5 L each, and dried at 50-53° C. (13-49 mbar) to afford crude (R)-2-butyl-3-hydroxypropionic acid (R)-α-methylbenzylammonium salt (5, 246.3 g; 41.7%); (R):(S)=94.1:5.9.

Crude (R)-2-butyl-3-hydroxypropionic acid (R)-α-methylbenzylammonium salt (5, 246.3 g) is transferred to a 5 L, 4-necked, round-bottomed flaks, equipped with a mechanical stirrer, digital thermometer, reflux condenser, addition funnel with nitrogen inlet-outlet and heating mantle. Ethyl acetate (1.225 L) and isopropanol (1.225 L) are then added. The suspension is stirred and heated to an internal temperature at 70-80° C. over a period of 1 hour to obtain a solution. The solution is cooled to 20-25° C. over a period of 2 hours and the resulting suspension is stirred at the same temperature for an additional 5 hours. The solids are collected by filtration, washed with a mixture of ethyl acetate-isopropanol (2:1 v/v) in two equal portions of 0.4 L each, and dried at 50-53° C. (13-49 mbar) to afford pure (R)-2-butyl-3-hydroxypropionic acid (R)-α-methylbenzylammonium salt (5, 215.6 g; 36.5%; 73.0% of theory); m.p. 145-147° C.; [α]$_D$+8.8 (c=1.0, CH$_3$OH); (R):(S)=99.3:0.7.

EXAMPLE 10

(R)-2-Butyl-3-hydroxypropionic acid (1)

(R)-2-Butyl-3-hydroxypropionic acid (R)-α-methylbenzylammonium salt (5, 10.0 g) is dissolved in 2 N HCl (40.0 mL) and isopropyl acetate (50.0 mL) is added to the mixture. After mixing for 5 min, the organic layer is separated and the aqueous layer is extracted with isopropyl acetate (3×50.0 mL). The combined organic layers are washed with water (20.0 mL) and concentrated under vacuum (20 mbar) until no further solvent distills to afford (R)-2-butyl-3-hydroxypropionic acid (1, 5.4 g, 98%); oil; [α]$_D$+6.5 (c=1.0, CH$_3$OH), (R):(S)=99.3:0.7.

EXAMPLE 11

(S)-2-Butyl-3-hydroxypropionic acid (S)-2-Butyl-3-hydroxypropionic acid is prepared by the resolution of (±)-2-butyl-3-hydroxypropionic acid (4) with (S)-α-methylbenzylamine in a similar manner as described above for the (R)-enantiomer. (S)-2-butyl-3-hydroxypropionic acid (S)-α-methylbenzylammonium salt, yield 33.2% (66.4% of theory); m.p. 145-147° C.; [α]$_D$-8.9 (c=1.0, CH$_3$OH); (S)-2-butyl-3-hydroxypropionic acid: yield 98%; oil; [α]$_D$-6.6 (c=1.0, CH$_3$OH); (R):(S)=0.4:99.6.

TABLE 1

Resolution of 4 (1.0 g) with (R)-α-methylbenzylamine (1.0 equiv)

| Entry | Solvent (ratio) | Solvent volume (mL/g of 4) | Enantiopurity of 5 (R):(S) | Isolated Yield (%) |
|---|---|---|---|---|
| 1 | CH$_3$CN:CH$_3$OH (75:25) | 13.6 | 85.6:14.4 | 31.0 |
| 2 | EtOAc:CH$_3$OH (70:30) | 10.0 | 96.0:4.0 | 26.7 |
| 3 | EtOAc:acetone (70:30) | 10.0 | 54.7:45.3 | 73.3 |
| 4 | EtOAc:C$_2$H$_5$OH (70:30) | 10.0 | 89.3:10.7 | 36.4 |

TABLE 1-continued

Resolution of 4 (1.0 g) with (R)-α-methylbenzylamine (1.0 equiv)

| Entry | Solvent (ratio) | Solvent volume (mL/g of 4) | Enantiopurity of 5 (R):(S) | Isolated Yield (%) |
|---|---|---|---|---|
| 5 | EtOAc:i-PrOH (50:50) | 12.0 | 94.1:5.9 | 41.7 |
|   | Recrystallization | 10.0 | 99.3:0.7 | 36.5 |

EXAMPLE 12

Displacement of Chiral Auxiliary with 4-methoxybenzyl Alcohol

To XIV (5.1 g, 11.6 mmol in THF (30 ml)) is added a mixture of 4-methoxybenzyl alcohol (1.93 g, 13.9 mmol), LiHMDS (1.95 g, 11.6 mmol) and tetrahydrofuran (40 mL) at 20° C. slowly and dropwise. The resulting mixture is stirred for 2 hours at 22° C. Ethyl acetate (150 mL) and 1 N HCl solution (40 mL) are added to the reaction mixture and the organic layer is separated. The organic layer is washed with water (50 mL), saturated NaHCO$_3$ solution (50 mL) and water (50 mL). The solvent is removed under reduced pressure to afford a crude product as an oil which is purified by flash chromatography on silica gel to give the desired XV (4-methoxybenzyl ester, 2.81 g, 60% yield).

EXAMPLE 13

Deprotection of 4-methoxybenzyl ester to (XIII)

A mixture of 4-methoxybenzyl ester, XV, (820 mg, 2.05 mmol) and formic acid (8 mL) is stirred at 22° C. for 2 hours. The reaction mixture is concentrated under reduced pressure. Ethyl acetate (50 mL) and 1 N Na$_2$CO$_3$ solution (15 mL) are added to the resulting residue and the aqueous layer is separated. The aqueous layer is acidified with 2 N HCl solution (10 mL) and extracted with ethyl acetate (2×30 mL). The organic layer is washed with water (20 mL). The solvent is removed under reduced pressure to afford a crude product as an oil which is purified by flash chromatography on silica gel to give the XIII (420 mg, 74% yield).

The examples 14 and 15 that follow make reference to reaction scheme below:

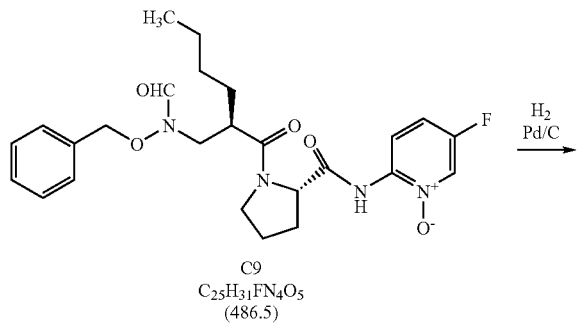

C9
C$_{25}$H$_{31}$FN$_4$O$_5$
(486.5)

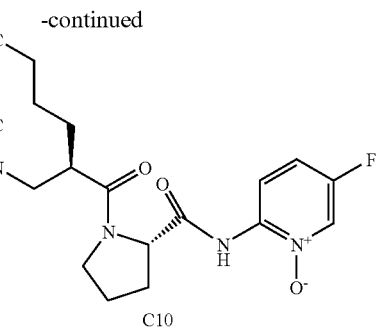

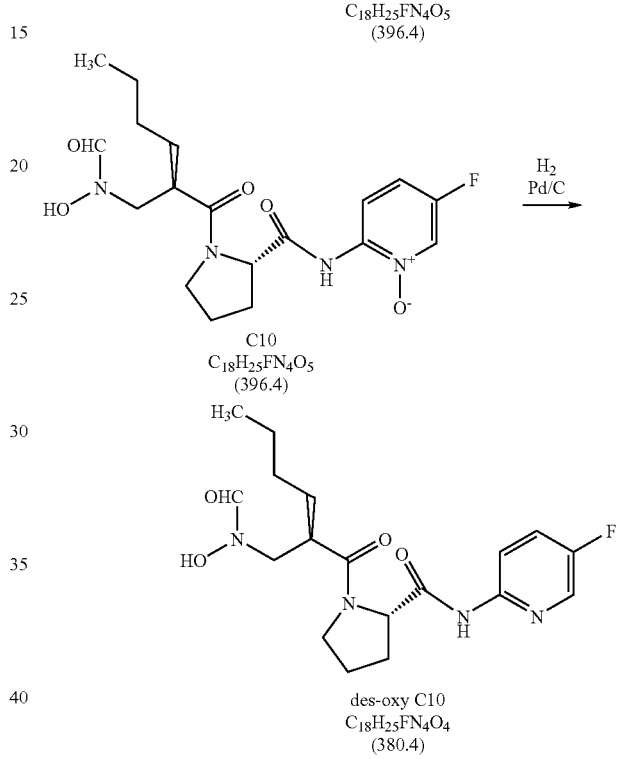

C10
C$_{18}$H$_{25}$FN$_4$O$_5$
(396.4)

C10
C$_{18}$H$_{25}$FN$_4$O$_5$
(396.4)

des-oxy C10
C$_{18}$H$_{25}$FN$_4$O$_4$
(380.4)

EXAMPLE 14

Debenzylation at Hydrogen Pressure of 0.24 atm

A means to operate at subatmospheric H$_2$ partial pressures while maintaining a total pressure of 1 atmosphere was achieved (thus obviating solvent evaporation and leaks) by performing the reaction using H$_2$ diluted with N$_2$). The apparatus comprises two calibrated mass flow controllers, one for N$_2$ and the other for H$_2$, which allow for a controlled flow rate of each gas based on an inputted set point. By varying the relative flow rates of the two gases, any H$_2$ partial pressure can be achieved. A 250-mL jacketed vessel equipped with a gassing agitator is charged with 8 g of C9, 62 g (~80 mL) of 200-proof ethanol, and 1.3 g of 5% Pd/C catalyst (Degussa, E1070 NO 5% Pd, water content 66.2 of wt %, Lot # 6JLG30), or 0.44 g of catalyst on a dry basis. The headspace is purged of air by flowing N$_2$ through both mass flow controllers at about 30 cm$^3$/min. The reactor is kept open to the atmospheric, giving a pressure of 1 atm in the vessel. The reaction is started by setting flow rates of 28 and 9 cm$^3$/min, respectively, on the N$_2$ and H$_2$ mass flow controllers, giving a H$_2$ partial pressure of 0.24 atm. A 700 rpm agitation rate is used, and the reaction temperature is 20° C. The lower hydrogen concentration in the liquid-phase gives a slower reaction, with the time required for 100% C9 conversion being about 3 h vs. 1.7 h for the 1-atm $H_2$ partial pressure case. A significant des-oxy C10 selectivity advantage is observed at 0.24 $H_2$ partial pressure. For example, a 0.99% des-oxy C10 yield is obtained at 97.6% C9 conversion, giving a selectivity of 1.01% vs. a des-oxy C10 yield of 6.07% at 99.8% C9 conversion, giving a selectivity of 6.1%, in the 1-atm case.

EXAMPLE 15

Debenzylation at a Hydrogen Partial Pressures of 0.1 atm

A 250-mL jacketed vessel equipped with a gassing agitator is charged with 8 g of C9, 62 g (~80 mL) of 200-proof ethanol, and 1.4 g of 5% Pd/C catalyst (Degussa, E1070 NO 5% Pd, water content 68.05 of wt %, Lot # CC1-2215), or 0.45 g of catalyst on a dry basis. The headspace is purged of air by flowing $N_2$ through both mass flow controllers at about 30 $cm^3$/min. The reactor is kept open to the atmospheric, giving a pressure of 1 atm in the vessel. The reaction is started by setting flow rates of 28 and 3 $cm^3$/min, respectively, on the $N_2$ and $H_2$ mass flow controllers, giving a $H_2$ partial pressure of 0.1 atm. A slower reaction is obtained relative to the 0.24 $H_2$ partial pressure case (4.5 vs. 3 h), but the reaction is not unreasonably long for a production process. Even more favorable des-oxy C10 selectivities are obtained at 0.1 atm $H_2$ partial pressure, viz., 0.78% des-oxy C10 yield at 99.8% C9 conversion, giving a des-oxy C10 selectivity of 0.78% vs. a 0.99% des-oxy C10 yield at 97.6% C9 conversion, giving a selectivity of 1.01%, for the 0.24-atm $H_2$ partial pressure case.

Example 16 makes reference to reaction scheme below:

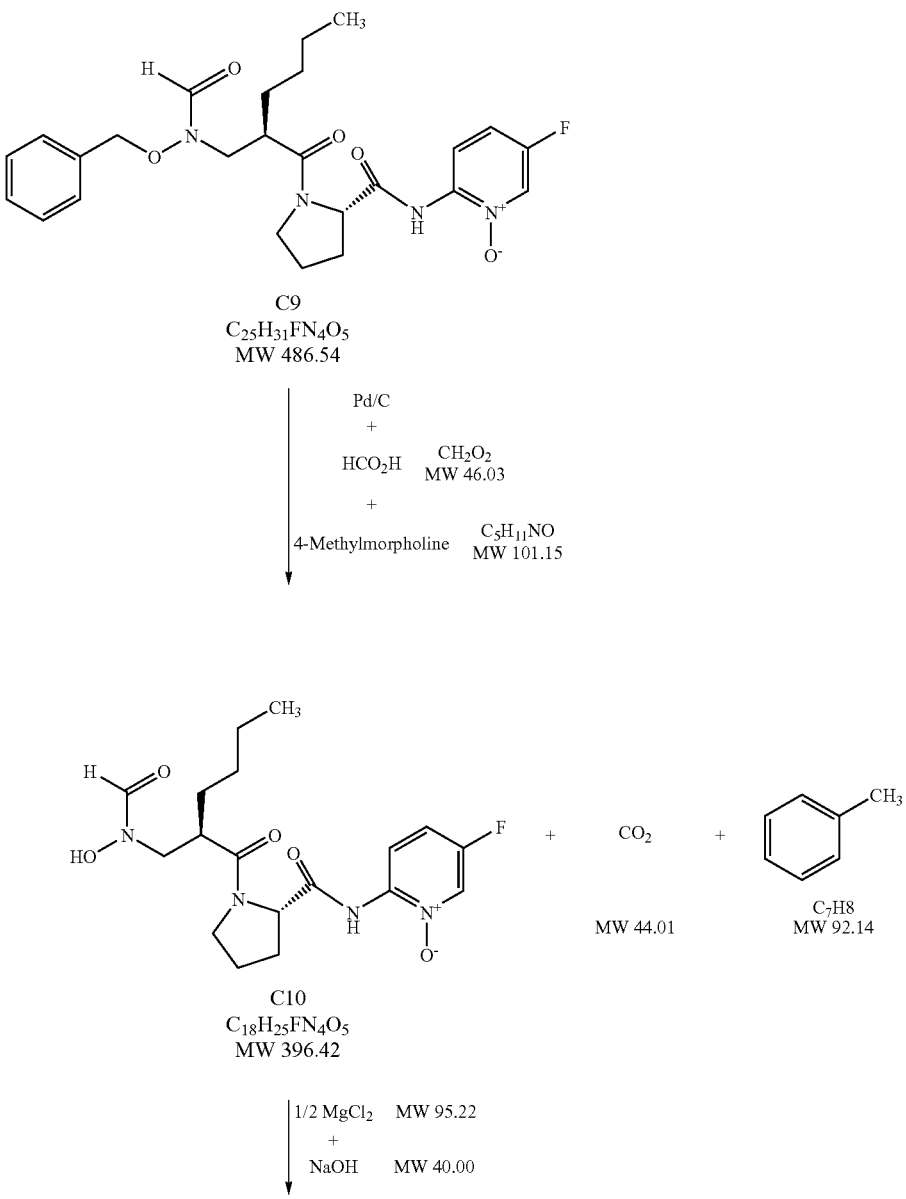

-continued

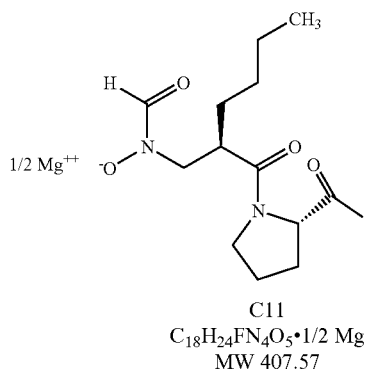

C11
$C_{18}H_{24}FN_4O_5 \cdot 1/2$ Mg
MW 407.57

EXAMPLE 16

A jacketed vessel is charged with 169.85 mmol solution of C9 in ethanol, 27.497 g of 4-methylmorpholine and 138.0 g of 200-proof ethanol. After stirring reaction mixture at about 22° C. 10.845 g of formic acid is added at a rate to maintain 22° C. following by addition of 69.0 g of 200-proof ethanol. 8.016 g of 10% Pd/C are added to the reaction following by addition of 44.28 g of 200-proof ethanol. Mixture is heated to about 45° C. for a period 25±10 min. Batch is held at this temperature for 2-3 hours. Filtered and twice washed with ethanol yielding C10.

What is claimed is:

1. A process for preparing a compound of formula (VIII)

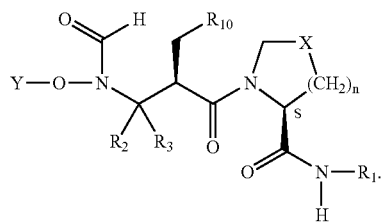

(VIII)

comprising Step A:

contacting a compound of formula (I)

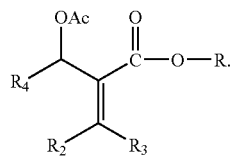

(I)

with a compound of the formula (II)

$Y-O-NH_2$ (II)

in a suitable solvent under conditions suitable to form a compound of the formula (III)

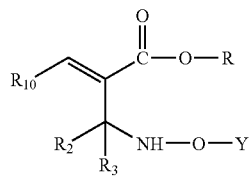

(III)

followed by asymmetric hydrogenation Step B:

contacting the compound of formula (III) with hydrogen in the presence of a chiral ligand and a catalytic amount of a hydrogenation catalyst in a suitable solvent and under conditions suitable to form a compound of the formula (IV)

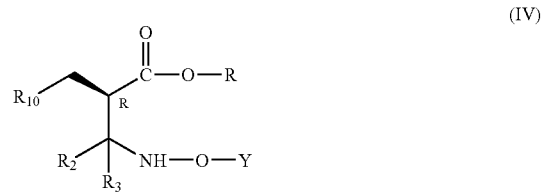

(IV)

followed by Step C:

contacting the compound of formula (IV) with a base such as a Grignard reagent in a suitable solvent under conditions suitable to form a compound of the formula (V)

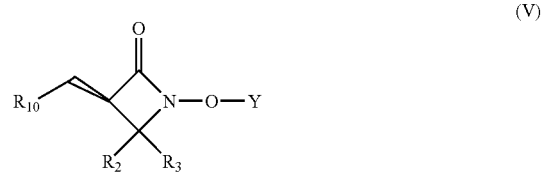

(V)

followed by Step D:

contacting the compound of formula (V) with a compound of the formula (VI)

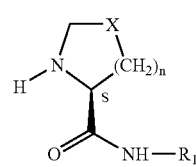

(VI)

in a suitable solvent, optionally in the presence of an activator under conditions suitable to form a compound of the formula (VII)

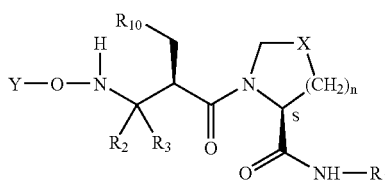

followed by Step E:
  contacting the compound of formula (VII) with a formylating agent in a suitable solvent under conditions suitable to form the compound of formula (VIII):
  wherein
    X is —$CH_2$—, —S—, —CH(OH)—, —CH(OR)—, —CH(SH)—, —CH(SR)—, —$CF_2$—, —C≡N(OR)— or —CH(F)—;
    Y is a hydroxyl-protecting group;
    R is alkyl;
    $R_1$ is aryl or heteroaryl;
    Ac is acetyl;
    each of $R_2$, $R_3$, and $R_{10}$ independently is hydrogen or alkyl, or ($R_2$ or $R_3$) collectively form a $C_4$-$C_7$cycloalkyl; and
    n is 0-3, provided that when n is 0, X is —$CH_2$—.

2. The process of claim 1 wherein $R_1$ is a heteroaryl of formula (II.1)

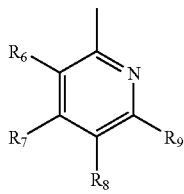

wherein
  $R_6$, $R_7$ and $R_9$ are hydrogen; and
  $R_8$ is methyl or trifluoromethyl; or
  $R_6$, $R_7$ and $R_8$ are hydrogen; and
  $R_9$ is fluoro; or
  $R_6$, $R_8$ and $R_9$ are hydrogen; and
  $R_7$ is ethyl or methoxy; or
  $R_7$, $R_8$ and $R_9$ are hydrogen; and
  $R_6$ is hydroxy; or
  $R_7$ and $R_8$ are hydrogen;
  $R_6$ is methoxy; and
  $R_9$ is methyl;
X is —$CH_2$—, —CH(OH)—, —CH(OR)—, —$CF_2$— or —CH(F)—, preferably X is —$CH_2$—;
$R_2$, $R_3$, $R_5$ are hydrogen;
$R_4$ is $C_1$-$C_6$alkyl; and
n is 1.

3. The process of claim 1 wherein $R_1$ is a heteroaryl of formula (III.1)

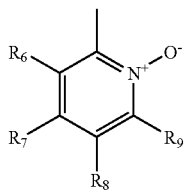

wherein
  $R_6$, $R_7$ and $R_9$ are hydrogen; and
  $R_8$ is fluoro or trifluoromethyl; or
  $R_6$, $R_8$ and $R_9$ are hydrogen; and
  $R_7$ is ethyl;
X is —$CH_2$—, —CH(OH)—, —CH(OR)—, —$CF_2$— or —CH(F)—, preferably X is —$CH_2$—;
$R_2$, $R_3$, $R_5$ are hydrogen;
$R_{10}$ is $C_1$-$C_5$alkyl; and
n is 1.

4. The process of claim 2 wherein
  $R_6$, $R_7$ and $R_9$ are hydrogen, $R_8$ is fluoro, X is —$CH_2$—; and $R_{10}$ is n-propyl.

5. The process of claim 1 wherein
  for Step A the temperature is about 10° C. to about 50° C. and the solvent is THF, DMF, or NMP,
  for Step B, the temperature is about 10° C. to about 50° C., the solvent is dioxane, methylene chloride, dichloromethane, toluene, acetone, methylethylketone, THF, isopropyl acetate, DMF, or an alcohols, the hydrogen is in the form of hydrogen gas, the pressure is about 40 psi to about 100 psi, the chiral ligand is (2S,5S)-Me-Duphos, or (1R,1'R,2S,2'S)-TangPhos, the amount of chiral ligand is about 1 mole % to about 15 mole % relative to the substrate, the hydrogenation catalyst is a transition metal complex containing rhodium (Rh I) or ruthenium (Ru II), the amount of catalyst is about 1 mole % to about 5 mole % relative to the substrate,
  for Step C the temperature is about −10° C. to about 20° C., the pH for Step C is about 8 pH to about 12 pH, the base is a Grignard reagent, the amount of Grignard reagent is about 1-5 equivalents relative to formula (IV), the solvent is acetone or methylethylketone,
  for Step D the temperature is about 30° C. to about 150° C., the pH for Step D is about 5 pH to about 11 pH, the activator, if present, is a branched or unbranched carboxylic acid, the solvent is an aqueous alcoholic solvent is selected from MeOH.$H_2O$, EtOH.$H_2O$, or the solvent is THF, dioxane or dimethoxyethane,
  for Step E the temperature is about −30° C. to about 50° C., the formylating agent is $HCO_2H/Ac_2O$, or trifluoroethylformate and the solvent is EtOAc, isopropylacetate, t-butylacetate or THF.

6. The process of claim 1 followed by the additional step of contacting the compound of formula (VIII) with hydrogen in the presence of a palladium catalyst to form a compound of formula (IX)

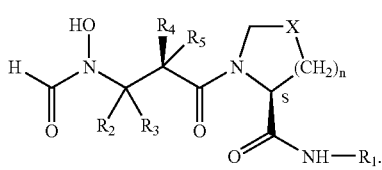

* * * * *